United States Patent [19]

Saville

[11] Patent Number: Plant 7,424

[45] Date of Patent: Jan. 22, 1991

[54] MINIATURE ROSE PLANT NAMED SAVABEAR

[75] Inventor: F. Harmon Saville, Rowley, Mass.

[73] Assignee: Nor'East Miniature Roses, Inc., Rowley, Mass.

[21] Appl. No.: 410,160

[22] Filed: Sep. 20, 1989

[51] Int. Cl.[5] ..... A01H 5/00

[52] U.S. Cl. ..... Plt./7

[58] Field of Search ..... Plt. 7, 10

*Primary Examiner*—Howard J. Locker

*Attorney, Agent, or Firm*—Christie, Parker & Hale

[57] ABSTRACT

A new and unusual orange brown russet miniature.

1 Drawing Sheet

SUMMARY OF THE INVENTION

The present invention relates to a new and distinct variety of rose plant of the miniature rose class, which was originated by my crossing as seed parent the variety known as "Sachet" (U.S. Plant Pat. No. 5,967) and as pollen parent the variety known as "Rainbow's End" (U.S. Plant Pat. No. 5,482). The varietal denomination of this new rose is "Savabear."

Among the novel characteristics possessed by this new variety which distinguishes it from its parents and all other varieties of which I am aware are its unusual orange brown colored (russet) flowers in this class of rose. Flowers open well and retain the unusual coloring. Asexual reproduction by propagation by cuttings of the new variety as performed in Essex County, Mass., shows that the foregoing and other distinguishing characteristics come true to form and are establsihed and transmitted through succeeding propagations.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Color Chart (RHSCC). The terminology used in the color description herein refers to plate numbers in the aforementioned color chart, e.g., "179A" is plate 179A of The Royal Horticultural Society Color Chart.

Parentage: Seedling.

*Seed parent.*—"Sachet".

*Pollen parent.*—"Rainbow's End".

Class: Miniature.

The following observations are made of specimens grown outdoors in Essex County, Mass., during the month of July.

FLOWER

Blooming habit: Continuous.

A. Bud: Continuous.

(1) *Size.*—Small.

(2) *Form.*—Ovate.

(3) *Color.*—As sepals divide, bud color is near 179A to B to 180B.

(4) *Sepals.*—About same length as bud.

(5) *Peduncle.*—Length — about ¾ inch. Aspect — straight. Strength — erect. Color — near 146C.

B. Bloom:

(1) *Size.*—Average size when fully expanded — about ¾ inch.

(2) *Borne.*—Sometimes, singly, one to a stem, but usually in sprays of 5 to 20 blooms.

(3) *Form.*—High centered at first, becoming flat. Petals sometimes undulate at margins and some roll under.

(4) *Petalage.*—Number of petals under normal conditions — about 28.

(5) *Color.*—After sepals fall and petals unfurl, predominant flower color viewing petals' top surface is near 179B to A; color of petal undersurface is of comparable orange brown tonality. General tonality at a distance is attractive russet coloring resembling light terra cotta. Color of petals at point of attachment is near 17A. As flowers age, orange brown coloring lightens to near 179D.

C. Petals:

(1) *Texture.*—Thick.

(2) *Appearance.*—Inside variety and outside satiny.

(3) *Form.*—Broad, fan shaped with pointed apices.

(4) *Arrangement.*—Regularly arranged, imbricated.

(5) *Petals in center.*—Few.

(6) *Persistence.*—Drop off cleanly.

(7) *Fragrance.*—Slight.

(8) *Lasting quality.*—Long lasting on plant and as cut flower.

REPRODUCTIVE ORGANS

A. Stamens, filaments and anthers:

*Arrangement and color.*—Regularly arranged around styles. Color — filaments near 23B.

B. Pollen:

*Color.*—Near 23B.

C. Styles: Even length.

D. Stigmas:

*Color.*—Near 4D.

E. Hips: Globular, medium size, color near 168C, seeds do not protrude.

PLANT

A. Form: Upright, compact.

B. Growth: Very vigorous.

*Height attained.*—About 14 to 16 inches.

C. Foliage: Compound 5 to 7 leaflets.

(1) *Size.*—Medium.

(2) *Quantity.*—Abundant.

(3) *Color.*—New foliage: Upper side — near 184A. Under side — near 184C. Old foliage: Upper side — near 137A. Under side — near 138B.

(4) *Shape.*—Oval, pointed.

(5) *Texture.*—Upper side is semi-glossy; under side is matte (6) *Edge.*—Serrate.

(7) *Serration.*—Small.

(8) *Leaf stem.*—Color — near 147C. Under side — near 137D.

(9) *Stipules.*—Medium length, slightly bearded.

(10) *Resistance to disease.*—Blackspot — average. Mildew — average. Rust — average.

D. Wood:

(1) *New wood.*—Color — near 182B. Bark — smooth.

(2) *Old wood.*—Color — near 143A. Bark — smooth.

E. Thorns:

(1) *Thorns.*—Quantity (main stalk) — ordinary. On laterals from stalk — few. Form — slightly curved downward. Length — medium. Color — near 185A. Position — irregular.

(2) *Prickles.*—None.

F. Winter hardiness: Needs protection in severe climates.

I claim:

1. A new and distinct variety of rose plant of the miniature rose class, substantially as shown and described, characterized particularly by attractive orange brown flowers.

* * * * *

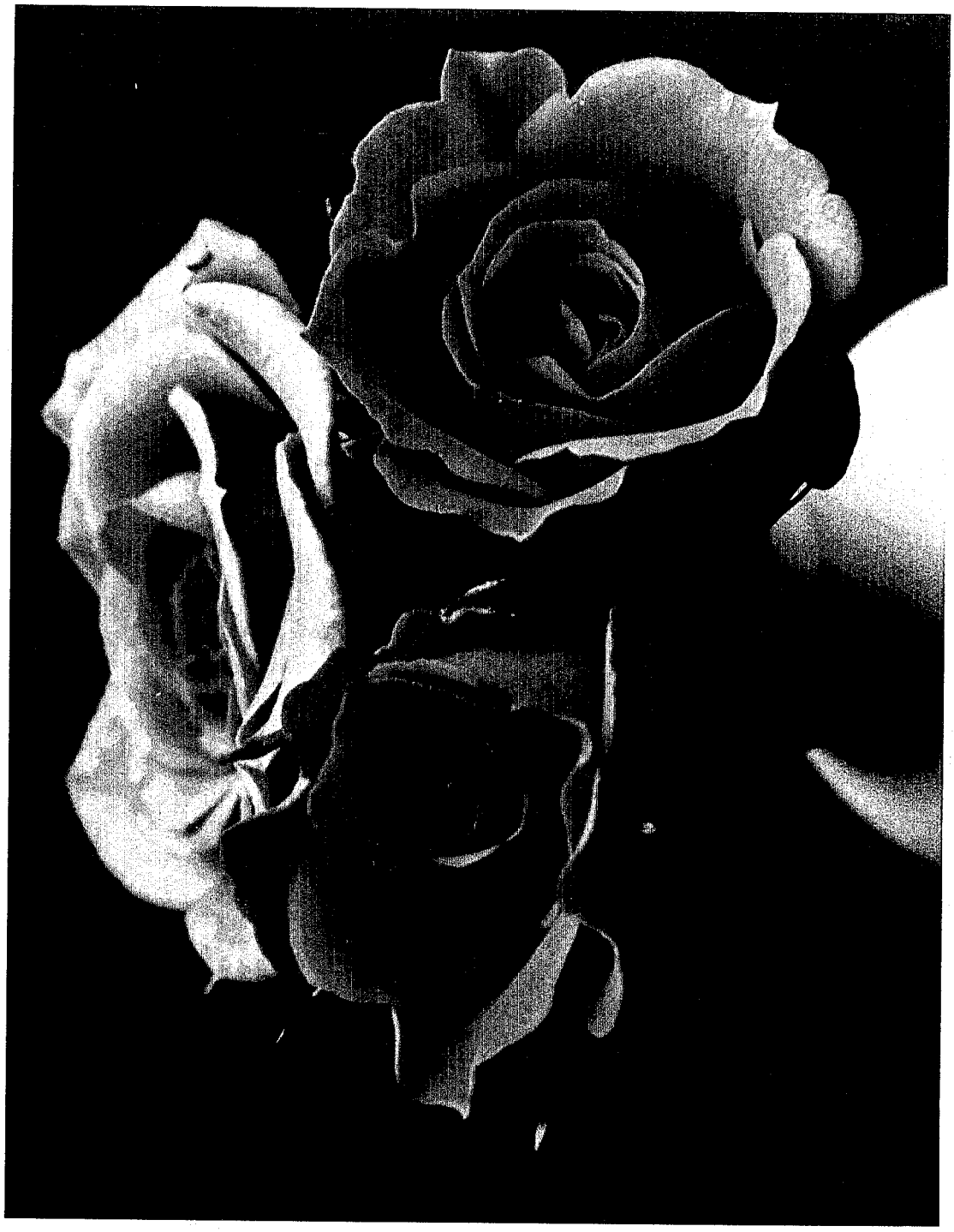

UNITED STATES PATENT AND TRADEMARK OFFICE

CERTIFICATE OF CORRECTION

PATENT NO. : Plant 7,424

DATED : January 22, 1991

INVENTOR(S) : F. Harmon Saville

It is certified that error appears in the above-identified patent and that said Letters Patent is hereby corrected as shown below:

Column 1, lines 18,19, change "establisihed" to -- established --.
Column 1, line 47, insert -- 1. -- before "FLOWER".

Column 2, line 28, change "variety" to -- velvety --.
Column 2, line 37, insert -- 2. -- before "REPRODUCTIVE ORGANS".
Column 2, line 49, insert -- 3. -- before "PLANT".

Signed and Sealed this

Third Day of November, 1992

*Attest:*

DOUGLAS B. COMER

*Attesting Officer*

*Acting Commissioner of Patents and Trademarks*